US006984727B1

(12) United States Patent
Hirochika et al.

(10) Patent No.: US 6,984,727 B1
(45) Date of Patent: Jan. 10, 2006

(54) GENE INVOLVED IN BRASSINOSTEROID RESPONSES

(75) Inventors: Hirohiko Hirochika, Ibaraki (JP); Muneo Yamazaki, Ibaraki (JP); Akio Miyao, Ibaraki (JP)

(73) Assignees: National Institute of Agrobiological Science, Tsukuba (JP); Bio-oriented Technology Research Advancement Institution, Saitama (JP)

( * ) Notice: Subject to any disclaimer, the term of this patent is extended or adjusted under 35 U.S.C. 154(b) by 0 days.

(21) Appl. No.: 09/721,114

(22) Filed: Nov. 22, 2000

(30) Foreign Application Priority Data

May 19, 2000 (JP) ............................. 2000-149106

(51) Int. Cl.
 *C12N 15/29* (2006.01)
(52) U.S. Cl. .................................... 536/23.6
(58) Field of Classification Search .............. 536/23.1, 536/24.3, 23.6; 800/278, 290; 435/468, 435/419
 See application file for complete search history.

(56) References Cited

U.S. PATENT DOCUMENTS 5,034,323 A 7/1991 Jorgensen et al. ........ 435/172.3

FOREIGN PATENT DOCUMENTS

WO WO 90/12084 10/1990

OTHER PUBLICATIONS

Saski et al. EMBL Accession AP001859, Apr. 20, 2000.*
Saski et al. GenBank Accession AP001859, May 27, 2000.*
Walbot (1992, Annu. Rev. Plant Physiol. Plant Mol. Biol. 43:49-82).*
Bowie et al, Science 247:1306-1310, 1990.*
McConnell et al, Nature 411 (6838):709-713, 2001.*
Noguchi et al (1999, Plant Physiology 121:743-752).*
Colliver et al (1997, Plant Mol. Biol. 35:509-522).*
Montgomery et al (Trends in Genetics, Jul. 1998, 14(7):255-258).*
Emery et al (2003, Current Biology 13:1768-1774).*
Altmann, "Recent Advances in Brassinosteroid Molecular Genetics," *Curr. Opin. Plant Biol.* 1:378-83 (1998).
Schumacher & Chory, "Brassinosteroid Signal Transduction: Still Casting the Actors," *Curr. Opin. Plant Biol.* 3:79-94 (2000).
Yamazaki et al. "Characterization of a rice stripe mutant induced by insertion of retrotransposon Tos17," Abstract 2P-0049, Program and Proceedings of 22nd Annual Meeting of the Molecular Biology Society of Japan (Nov. 22, 1999) (translation enclosed).

* cited by examiner

*Primary Examiner*—Amy J. Nelson
*Assistant Examiner*—Stuart F. Baum
(74) *Attorney, Agent, or Firm*—James F. Haley, Jr.; Fish & Neave IP Group, Ropes & Gray LLP

(57) ABSTRACT

There is provided a polynucleotide encoding a plant gene capable of controlling a signal transduction system for brassinosteroid hormone, the polynucleotide encoding an amino acid sequence from Met at position 1 to Arg at position 1057 of SEQ ID NO: 2 in the SEQUENCE LISTING, including any polynucleotide encoding an amino acid sequence in which one or more amino acids are deleted, substituted or added to the amino acid sequence.

2 Claims, 7 Drawing Sheets

A Mutant (A0369 -/-) Wild Type (Akitakomachi)
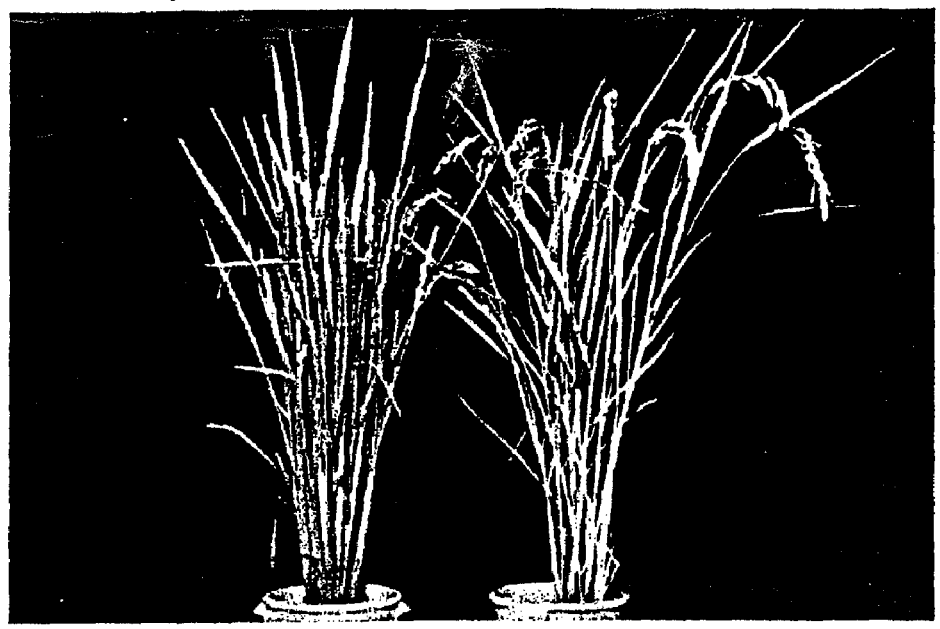
B Mutant (A0369 -/-) Wild Type (Akitakomachi)
Fig. 1

A  Mutant    Wild Type
B  Mutant                              Wild Type
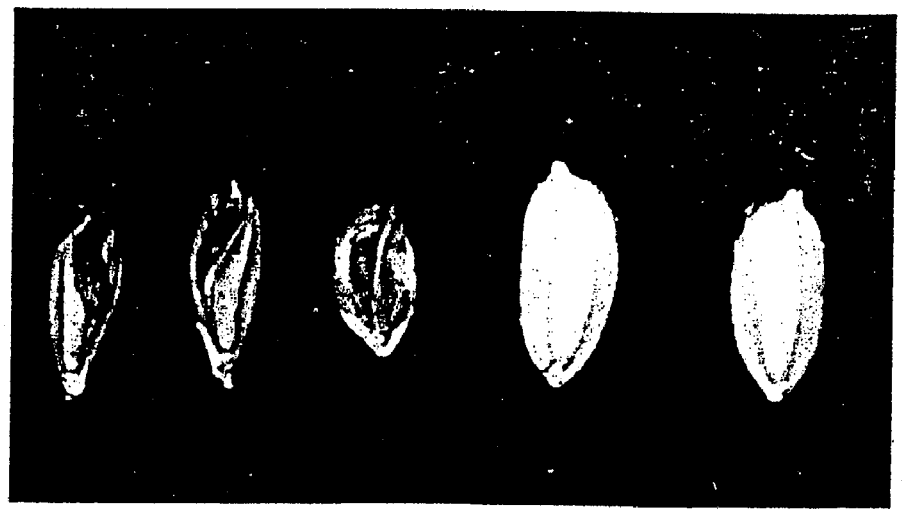
Fig. 2

| | | | | | |
|---|---|---|---|---|---|
| MEIVAVDQEG | ARVVGTNCML | ARGGTGAVAP | VLELTATPRQ | DAAAEAGVDE | 50 |
| PAQHQCEHFS | IRGYVALLQK | KDPKFCSLSR | IFHDQKKCDE | HKASSSPFSV | 100 |
| AKFRRWDCSK | CLDKLKTSDN | GTAPRTLPAK | QNGTSDGCSI | TFVRSTFVPA | 150 |
| SVGSQKVSPS | TQSSQGKNAD | RSTLPKSVQE | GNDSKCNAPS | GKNGAAEANT | 200 |
| DSPMKDLQGP | AQNYDVAANV | SEDNTSVDVG | ALPEVPQITW | HIEVNGADQP | 250 |
| PSTPKLSEVV | LKRNEDENGK | TEETLVAEQC | NLTKDPNPMS | GKERDQVAEQ | 300 |
| CNLTKDPKPV | SGQKCEQICN | EPCEEVVLKR | SSKSKRKTDK | KLMKKQQHSK | 350 |
| KRTAQADVSD | AKLCRRKPKK | VRLLSEIINA | NQVEDSRSDE | VHRENAADPC | 400 |
| EDDRSTIPVP | MEVSMDIPVS | NHTVGEDGLK | SSKNKTKRKY | SDVVDDGSSL | 450 |
| MNWLNGKKKR | TGSVHHTVAH | PAGNLSNKKV | TPTASTQHDD | ENDTENGLDT | 500 |
| NMHKTDVCQH | VSEISTQRCS | SKGKTAGLSK | GKVHSAASTK | YGGESTRNGQ | 550 |
| NIHVLSAEDQ | CQMETENSVL | SHSAKVSPAE | HDKQIMSDLH | EQSLPKKKKK | 600 |
| QKLEVTREKQ | TMIDDIPMDI | VELLAKNQHE | RQLMTEKDCS | DINRIQSKTT | 650 |
| ADDDCVIVAA | KDGSDYASSV | FDTNSQQKSL | ASQSTQKELQ | GHLALTTQES | 700 |
| PHPQNFQSTQ | EQQTHLRMEE | MVTIAASSPL | FSHHDDQYIA | EAPKEHWGRK | 750 |
| DAKKLTWEQF | KATTRNSPAA | TCGAQFRPGI | QAVDLTSTHV | MGSSSNYASR | 800 |
| QPVIAPLDRY | AERAVNQVHA | RNFPSTIATM | EASKLCDRRN | AGQVVLYPKE | 850 |
| SMPATHLLRM | MDPSTLASFP | NYGTSSRNQM | ESQLHNSQYA | HNQYKGSTST | 900 |
| SYGSNLNGKI | PLTFEDLSRH | QLHDLHRPLR | PHPRVGVLGS | LLQKEIANWS | 950 |
| ENCGTQSGYK | LGVSTGITSH | QMNRKEHFEA | LNSGMFSAKW | NALQLGSVSS | 1000 |
| SADFLSARNS | IAQSWTRGKG | KMVHPLDRFV | RQDICITNKN | PADFTTISND | 1050 |
| NEYMDYR | 1057 | | | | |

Nuclear localization signal (1)

Nuclear localization signal (2)

ATP/GTP binding motif

SEQUENCE LISTING

```
<160> NUMBER OF SEQ ID NOS: 5

<210> SEQ ID NO 1
<211> LENGTH: 4310
<212> TYPE: DNA
<213> ORGANISM: Oryza sativa
<220> FEATURE:
<221> NAME/KEY: CDS
<222> LOCATION: (655)..(3828)

<400> SEQUENCE: 1
ctcttctcca ctccaaatcc cttcttaccc tattccctc cccccgcagc ttctcttcct      60
cctgcagtac tcgccgccac caccaccgcg ccgccgccgc cggccgcgtt ccgagaccca     120
ctcgatcgga atccaccgcg gcgcgcccgc gcgcctgcgt cctcttcctt ccccgggagc     180
cgaccgacca cggcgaccag tcgatctccc tctccgggcg ccaaccgcgt cttagcttca     240
tcgaatccac cgccccaccc cgcatctcct cctcctcctc cgacgacgac gactactact     300
agtcttctcc aataagcccc cctcccgctc cccccgcctg aagaagaagc agcagctagc     360
tccggggaga ggtcgacggc gcgccgggta gatcgcgccc cgcccgcct gcgtcgcggc     420 tgtcggagca aacgcaaacc ccccaggttg ttctagcgtg tgcagcggct agctgattga     480
ttgtcttctg tgatatatcc agagctcgtg ttttgtggtt tgtggtttgt ggtttgtgct     540
tggattgttg atgtgctaat tcgcggcgtt acaagatcac tgctggattg atattgagtt     600
gtgcctcggc tgtgctagct gtgtgttgat tctctcctcg tcgtggtgat cgat atg        657
                                                                 Met
                                                                  1 gag att gtt gca gta gat cag gag gga gct cgt gtt gtt ggg acg aac        705
Glu Ile Val Ala Val Asp Gln Glu Gly Ala Arg Val Val Gly Thr Asn
          5                  10                  15 tgt atg ctt gct cgt ggt gga act ggt gct gta gcg cca gtg ttg gag        753
Cys Met Leu Ala Arg Gly Gly Thr Gly Ala Val Ala Pro Val Leu Glu
     20                  25                  30 ctg aca gcg acg cct cgt cag gat gca gcc gct gaa gct ggt gta gac        801
Leu Thr Ala Thr Pro Arg Gln Asp Ala Ala Ala Glu Ala Gly Val Asp
 35                  40                  45 gaa ccg gca caa cac caa tgc gag cat ttc tcc ata aga ggg tat gtt        849
Glu Pro Ala Gln His Gln Cys Glu His Phe Ser Ile Arg Gly Tyr Val
 50                  55                  60                  65 gct ctt ctt cag aag aag gat cca aaa ttc tgc tct cta tct cgg att        897
Ala Leu Leu Gln Lys Lys Asp Pro Lys Phe Cys Ser Leu Ser Arg Ile
             70                  75                  80
```

-continued

```
ttc cat gac cag aaa aaa tgt gat gaa cac aaa gct agt tca agc cca        945
Phe His Asp Gln Lys Lys Cys Asp Glu His Lys Ala Ser Ser Ser Pro
            85                  90                  95 ttt tct gta gca aag ttt cga cga tgg gat tgc tcg aag tgc ttg gat        993
Phe Ser Val Ala Lys Phe Arg Arg Trp Asp Cys Ser Lys Cys Leu Asp
        100                 105                 110 aag ttg aaa act tca gat aat gga aca gca cca aga act ctt ccc gca       1041
Lys Leu Lys Thr Ser Asp Asn Gly Thr Ala Pro Arg Thr Leu Pro Ala
    115                 120                 125 aag cag aat ggc aca agt gat ggt tgc tcc atc aca ttt gtt cgg agc       1089
Lys Gln Asn Gly Thr Ser Asp Gly Cys Ser Ile Thr Phe Val Arg Ser
130                 135                 140                 145 act ttt gtg cct gct agt gtt ggt tcc caa aaa gtg tct cct agc aca       1137
Thr Phe Val Pro Ala Ser Val Gly Ser Gln Lys Val Ser Pro Ser Thr
                150                 155                 160 caa tca tct caa ggg aag aat gct gat aga tca act ctt cca aag agt       1185
Gln Ser Ser Gln Gly Lys Asn Ala Asp Arg Ser Thr Leu Pro Lys Ser
            165                 170                 175 gtg caa gaa ggc aat gac tcc aaa tgc aat gcg cct tct ggc aag aat       1233
Val Gln Glu Gly Asn Asp Ser Lys Cys Asn Ala Pro Ser Gly Lys Asn
        180                 185                 190 gga gct gct gag gcc aat act gat tca cca atg aaa gat ttg caa ggg       1281
Gly Ala Ala Glu Ala Asn Thr Asp Ser Pro Met Lys Asp Leu Gln Gly
    195                 200                 205 cca gcc caa aat tat gat gtg gca gca aat gtc tct gag gac aac act       1329
Pro Ala Gln Asn Tyr Asp Val Ala Ala Asn Val Ser Glu Asp Asn Thr
210                 215                 220                 225 tct gtt gat gtt ggg gct tta cct gaa gtt ccc cag att aca tgg cac       1377
Ser Val Asp Val Gly Ala Leu Pro Glu Val Pro Gln Ile Thr Trp His
                230                 235                 240 ata gaa gta aat ggt gca gat caa cct cca tcc act cca aaa ctt tct       1425
Ile Glu Val Asn Gly Ala Asp Gln Pro Pro Ser Thr Pro Lys Leu Ser
            245                 250                 255 gaa gtg gtc ctc aaa aga aat gaa gat gaa aat gga aaa act gaa gag       1473
Glu Val Val Leu Lys Arg Asn Glu Asp Glu Asn Gly Lys Thr Glu Glu
        260                 265                 270 act ctt gtt gct gag cag tgc aat ttg acc aaa gat cct aac cca atg       1521
Thr Leu Val Ala Glu Gln Cys Asn Leu Thr Lys Asp Pro Asn Pro Met
    275                 280                 285 tct gga aag gaa cgt gat cag gtt gct gag cag tgc aat ttg acc aaa       1569
Ser Gly Lys Glu Arg Asp Gln Val Ala Glu Gln Cys Asn Leu Thr Lys
290                 295                 300                 305 gat ccg aaa cca gtg tct ggg cag aaa tgt gag cag atc tgc aat gag       1617
Asp Pro Lys Pro Val Ser Gly Gln Lys Cys Glu Gln Ile Cys Asn Glu
                310                 315                 320 cca tgt gaa gaa gtt gtt ctc aaa aga agc tcc aaa tct aag agg aag       1665
Pro Cys Glu Glu Val Val Leu Lys Arg Ser Ser Lys Ser Lys Arg Lys
            325                 330                 335 acg gat aag aag ttg atg aag aag cag cag cac agc aag aaa cgc act       1713
Thr Asp Lys Lys Leu Met Lys Lys Gln Gln His Ser Lys Lys Arg Thr
        340                 345                 350 gcc cag gct gat gtt tca gat gca aag ctt tgt cgg aga aag cca aaa       1761
Ala Gln Ala Asp Val Ser Asp Ala Lys Leu Cys Arg Arg Lys Pro Lys
    355                 360                 365 aag gtg cgg ctt cta tca gaa att ata aat gct aac cag gtt gag gat       1809
Lys Val Arg Leu Leu Ser Glu Ile Ile Asn Ala Asn Gln Val Glu Asp
370                 375                 380                 385 tct aga agt gac gaa gtt cat cgt gaa aat gcc gct gat ccc tgt gag       1857
Ser Arg Ser Asp Glu Val His Arg Glu Asn Ala Ala Asp Pro Cys Glu
```

-continued

```
                        390                   395                   400
gat gat aga agt acc atc ccg gtc ccg atg gaa gta agc atg gat att    1905
Asp Asp Arg Ser Thr Ile Pro Val Pro Met Glu Val Ser Met Asp Ile
                405                   410                   415 cct gtt agc aac cat aca gtg gga gaa gat ggg tta aaa tca agt aag    1953
Pro Val Ser Asn His Thr Val Gly Glu Asp Gly Leu Lys Ser Ser Lys
                420                   425                   430 aac aag aca aaa cgc aaa tac tct gat gtt gta gat gat gga tca tca    2001
Asn Lys Thr Lys Arg Lys Tyr Ser Asp Val Val Asp Asp Gly Ser Ser
        435                   440                   445 ctt atg aac tgg ctg aat gga aaa aag aaa aga act gga agt gtg cat    2049
Leu Met Asn Trp Leu Asn Gly Lys Lys Lys Arg Thr Gly Ser Val His
450                   455                   460                   465 cac aca gtt gct cat cca gct ggg aat ttg agc aac aaa aaa gtg aca    2097
His Thr Val Ala His Pro Ala Gly Asn Leu Ser Asn Lys Lys Val Thr
                470                   475                   480 ccc act gcg agt act cag cat gat gat gag aat gat act gaa aat ggt    2145
Pro Thr Ala Ser Thr Gln His Asp Asp Glu Asn Asp Thr Glu Asn Gly
                485                   490                   495 ctt gac aca aat atg cat aag aca gat gtc tgt cag cat gta tca gaa    2193
Leu Asp Thr Asn Met His Lys Thr Asp Val Cys Gln His Val Ser Glu
        500                   505                   510 atc tcc aca cag agg tgc tca tca aag ggg aaa aca gcg ggt ttg agt    2241
Ile Ser Thr Gln Arg Cys Ser Ser Lys Gly Lys Thr Ala Gly Leu Ser
515                   520                   525 aag ggg aaa aca cat tca gct gct agt acc aaa tat ggt ggt gaa agc    2289
Lys Gly Lys Thr His Ser Ala Ala Ser Thr Lys Tyr Gly Gly Glu Ser
530                   535                   540                   545 acc aga aat ggt cag aac ata cat gta ctc agc gca gaa gat caa tgc    2337
Thr Arg Asn Gly Gln Asn Ile His Val Leu Ser Ala Glu Asp Gln Cys
                550                   555                   560 cag atg gaa acc gaa aac tct gtt ctg agt cac tcg gca aag gtt tct    2385
Gln Met Glu Thr Glu Asn Ser Val Leu Ser His Ser Ala Lys Val Ser
                565                   570                   575 cca gct gag cat gat atc caa att atg tct gac ctt cat gag cag agt    2433
Pro Ala Glu His Asp Ile Gln Ile Met Ser Asp Leu His Glu Gln Ser
                580                   585                   590 cta ccc aag aag aaa aag aag caa aaa ctt gaa gtg act cgt gaa aaa    2481
Leu Pro Lys Lys Lys Lys Lys Gln Lys Leu Glu Val Thr Arg Glu Lys
595                   600                   605 cag acc atg ata gat gac atc ccc atg gat att gtt gaa ctg cta gct    2529
Gln Thr Met Ile Asp Asp Ile Pro Met Asp Ile Val Glu Leu Leu Ala
610                   615                   620                   625 aaa aac cag cat gag agg cag ctt atg act gag act gat tgt tct gac    2577
Lys Asn Gln His Glu Arg Gln Leu Met Thr Glu Thr Asp Cys Ser Asp
                630                   635                   640 atc aac cgt att caa tcc aag aca act gct gat gat gat tgt gta ata    2625
Ile Asn Arg Ile Gln Ser Lys Thr Thr Ala Asp Asp Asp Cys Val Ile
                645                   650                   655 gta gct gcc aag gat ggt tca gat tat gca tca agt gtg ttt gac act    2673
Val Ala Ala Lys Asp Gly Ser Asp Tyr Ala Ser Ser Val Phe Asp Thr
                660                   665                   670 aat tcc caa cag aag tcc ttg gca tcc caa agt aca cag aag gag tta    2721
Asn Ser Gln Gln Lys Ser Leu Ala Ser Gln Ser Thr Gln Lys Glu Leu
        675                   680                   685 cag ggt cat ttg gca ttg acc aca caa gag tct cca cat cct cag aac    2769
Gln Gly His Leu Ala Leu Thr Thr Gln Glu Ser Pro His Pro Gln Asn
690                   695                   700                   705 ttt cag tct act cag gaa cag cag aca cat ttg cgg atg gaa gaa atg    2817
```

```
                Phe Gln Ser Thr Gln Glu Gln Gln Thr His Leu Arg Met Glu Glu Met
                            710                 715                 720 gtc act att gct gca agc tca cca cta ttt tca cat cat gat gat cag           2865
Val Thr Ile Ala Ala Ser Ser Pro Leu Phe Ser His His Asp Asp Gln
            725                 730                 735 tat att gct gaa gca cca act gaa cat tgg ggc cgt aag gac gca aag           2913
Tyr Ile Ala Glu Ala Pro Thr Glu His Trp Gly Arg Lys Asp Ala Lys
            740                 745                 750 aag cta acg tgg gag caa ttt aag gcc act aca aga aat tct cca gca           2961
Lys Leu Thr Trp Glu Gln Phe Lys Ala Thr Thr Arg Asn Ser Pro Ala
            755                 760                 765 gca aca tgt ggt gct caa ttt aga cct ggt atc caa gca gtt gac ttg           3009
Ala Thr Cys Gly Ala Gln Phe Arg Pro Gly Ile Gln Ala Val Asp Leu
770                 775                 780                 785 act tct act cat gtc atg gga tct tcc agc aat tat gca tct cgc caa           3057
Thr Ser Thr His Val Met Gly Ser Ser Ser Asn Tyr Ala Ser Arg Gln
                790                 795                 800 cca gta att gcg cca ctg gac cgc tat gct gaa aga gcg gtt aac cag           3105
Pro Val Ile Ala Pro Leu Asp Arg Tyr Ala Glu Arg Ala Val Asn Gln
            805                 810                 815 gtc cat gca aga aat ttt cca agc aca ata gca acc atg gaa gcg agt           3153
Val His Ala Arg Asn Phe Pro Ser Thr Ile Ala Thr Met Glu Ala Ser
            820                 825                 830 aag tta tgt gat cgg aga aat gct gga caa gta gtc ttg tat cct aaa           3201
Lys Leu Cys Asp Arg Arg Asn Ala Gly Gln Val Val Leu Tyr Pro Lys
835                 840                 845 gaa tcc atg cct gcg acg cat ctt ctg aga atg atg gat cca tca aca           3249
Glu Ser Met Pro Ala Thr His Leu Leu Arg Met Met Asp Pro Ser Thr
850                 855                 860                 865 tta gca agc ttc ccc aac tat gga act tct agc agg aac cag atg gag           3297
Leu Ala Ser Phe Pro Asn Tyr Gly Thr Ser Ser Arg Asn Gln Met Glu
                870                 875                 880 tct caa ctt cat aat tct cag tat gca cat aat cag tac aaa gga tca           3345
Ser Gln Leu His Asn Ser Gln Tyr Ala His Asn Gln Tyr Lys Gly Ser
            885                 890                 895 acc agc aca tca tat ggc agt aac ctg aat gga aag att cca ttg aca           3393
Thr Ser Thr Ser Tyr Gly Ser Asn Leu Asn Gly Lys Ile Pro Leu Thr
            900                 905                 910 ttc gaa gac tta tca cgg cat cag ctg cat gat ctg cac aga cct tta           3441
Phe Glu Asp Leu Ser Arg His Gln Leu His Asp Leu His Arg Pro Leu
            915                 920                 925 cgc cca cat cct aga gtt ggt gtg ctt ggc tcc ttg ctg cag aag gaa           3489
Arg Pro His Pro Arg Val Gly Val Leu Gly Ser Leu Leu Gln Lys Glu
930                 935                 940                 945 att gca aac tgg tcg gag aac tgt ggc aca caa tct ggt tat aag tta           3537
Ile Ala Asn Trp Ser Glu Asn Cys Gly Thr Gln Ser Gly Tyr Lys Leu
                950                 955                 960 gga gtg tca aca gga ata aca tcg cat cag atg aac aga aag gaa cat           3585
Gly Val Ser Thr Gly Ile Thr Ser His Gln Met Asn Arg Lys Glu His
            965                 970                 975 ttt gaa gcc ctg aat tct gga atg ttt tca gca aaa tgg aat gca ttg           3633
Phe Glu Ala Leu Asn Ser Gly Met Phe Ser Ala Lys Trp Asn Ala Leu
            980                 985                 990 cag ttg ggt tct gtt agc tcc agt gca gat ttt tta tca gcg agg aac           3681
Gln Leu Gly Ser Val Ser Ser Ser Ala Asp Phe Leu Ser Ala Arg Asn
            995                 1000                1005 agc ata gct caa tct tgg acc aga ggc aag ggt aaa atg gtt cat ccc           3729
Ser Ile Ala Gln Ser Trp Thr Arg Gly Lys Gly Lys Met Val His Pro
1010                1015                1020                1025
```

-continued

| | |
|---|---|
| ttg gat cgg ttt gtg aga cag gat atc tgt ata act aac aag aac cca<br>Leu Asp Arg Phe Val Arg Gln Asp Ile Cys Ile Thr Asn Lys Asn Pro<br>            1030                    1035                    1040 | 3777 |
| gct gat ttt act aca atc agt aac gat aac gag tat atg gat tac cgc<br>Ala Asp Phe Thr Thr Ile Ser Asn Asp Asn Glu Tyr Met Asp Tyr Arg<br>            1045                    1050                    1055 | 3825 |
| tga agcagaaagt ggtgtgcata attcctgaac atttacaatc atacatttca | 3878 |
| tctttatggc gccaaatagt catactgtaa gaggagggct tgctggatc tgctgtaagg | 3938 |
| cttcttgtaa gttgtggatg ccccattttc tggatgggaa cctgccagac agtgaacaag | 3998 |
| ggctttgcaa ggtgcagcat ccggttttg ttttgccagt ccaagaaacg tcctcctgtt | 4058 |
| actttgtagt tgtactcata ctagtgcgct tgtttgtaca aggagaaatg tgtaaccttg | 4118 |
| ttgaaaaaat gtctccccca ttttgtaatt accataagga ggtttatagt gttgtgagct | 4178 |
| gtgtgtgact gacggcgaga atggttttg tcggtgttaa ggttgaaacg actagctctc | 4238 |
| gttatcaatg tgttgtaaac ttctagattg atgtgttacc ttactcttga agtcaacacc | 4298 |
| ggagaattta ca | 4310 |

<210> SEQ ID NO 2
<211> LENGTH: 1057
<212> TYPE: PRT
<213> ORGANISM: Oryza sativa

<400> SEQUENCE: 2

Met Glu Ile Val Ala Val Asp Gln Glu Gly Ala Arg Val Val Gly Thr
1               5                   10                  15

Asn Cys Met Leu Ala Arg Gly Gly Thr Gly Ala Val Ala Pro Val Leu
            20                  25                  30

Glu Leu Thr Ala Thr Pro Arg Gln Asp Ala Ala Glu Ala Gly Val
        35                  40                  45

Asp Glu Pro Ala Gln His Gln Cys Glu His Phe Ser Ile Arg Gly Tyr
    50                  55                  60

Val Ala Leu Leu Gln Lys Lys Asp Pro Lys Phe Cys Ser Leu Ser Arg
65                  70                  75                  80

Ile Phe His Asp Gln Lys Lys Cys Asp Glu His Lys Ala Ser Ser Ser
                85                  90                  95

Pro Phe Ser Val Ala Lys Phe Arg Arg Trp Asp Cys Ser Lys Cys Leu
            100                 105                 110

Asp Lys Leu Lys Thr Ser Asp Asn Gly Thr Ala Pro Arg Thr Leu Pro
        115                 120                 125

Ala Lys Gln Asn Gly Thr Ser Asp Gly Cys Ser Ile Thr Phe Val Arg
    130                 135                 140

Ser Thr Phe Val Pro Ala Ser Val Gly Ser Gln Lys Val Ser Pro Ser
145                 150                 155                 160

Thr Gln Ser Ser Gln Gly Lys Asn Ala Asp Arg Ser Thr Leu Pro Lys
                165                 170                 175

Ser Val Gln Glu Gly Asn Asp Ser Lys Cys Asn Ala Pro Ser Gly Lys
            180                 185                 190

Asn Gly Ala Ala Glu Ala Asn Thr Asp Ser Pro Met Lys Asp Leu Gln
        195                 200                 205

Gly Pro Ala Gln Asn Tyr Asp Val Ala Ala Asn Val Ser Glu Asp Asn
    210                 215                 220

Thr Ser Val Asp Val Gly Ala Leu Pro Glu Val Pro Gln Ile Thr Trp
225                 230                 235                 240

-continued

```
His Ile Glu Val Asn Gly Ala Asp Gln Pro Pro Ser Thr Pro Lys Leu
                245                 250                 255

Ser Glu Val Val Leu Lys Arg Asn Glu Asp Glu Asn Gly Lys Thr Glu
            260                 265                 270

Glu Thr Leu Val Ala Glu Gln Cys Asn Leu Thr Lys Asp Pro Asn Pro
        275                 280                 285

Met Ser Gly Lys Glu Arg Asp Gln Val Ala Glu Gln Cys Asn Leu Thr
    290                 295                 300

Lys Asp Pro Lys Pro Val Ser Gly Gln Lys Cys Glu Gln Ile Cys Asn
305                 310                 315                 320

Glu Pro Cys Glu Glu Val Leu Lys Arg Ser Ser Lys Ser Lys Arg
                325                 330                 335

Lys Thr Asp Lys Lys Leu Met Lys Lys Gln Gln His Ser Lys Lys Arg
                340                 345                 350

Thr Ala Gln Ala Asp Val Ser Asp Ala Lys Leu Cys Arg Arg Lys Pro
                355                 360                 365

Lys Lys Val Arg Leu Leu Ser Glu Ile Ile Asn Ala Asn Gln Val Glu
            370                 375                 380

Asp Ser Arg Ser Asp Glu Val His Arg Glu Asn Ala Ala Asp Pro Cys
385                 390                 395                 400

Glu Asp Asp Arg Ser Thr Ile Pro Val Pro Met Glu Val Ser Met Asp
                405                 410                 415

Ile Pro Val Ser Asn His Thr Val Gly Glu Asp Gly Leu Lys Ser Ser
                420                 425                 430

Lys Asn Lys Thr Lys Arg Lys Tyr Ser Asp Val Val Asp Asp Gly Ser
            435                 440                 445

Ser Leu Met Asn Trp Leu Asn Gly Lys Lys Arg Thr Gly Ser Val
    450                 455                 460

His His Thr Val Ala His Pro Ala Gly Asn Leu Ser Asn Lys Lys Val
465                 470                 475                 480

Thr Pro Thr Ala Ser Thr Gln His Asp Asp Glu Asn Asp Thr Glu Asn
                485                 490                 495

Gly Leu Asp Thr Asn Met His Lys Thr Asp Val Cys Gln His Val Ser
                500                 505                 510

Glu Ile Ser Thr Gln Arg Cys Ser Ser Lys Gly Lys Thr Ala Gly Leu
            515                 520                 525

Ser Lys Gly Lys Thr His Ser Ala Ala Ser Thr Lys Tyr Gly Gly Glu
    530                 535                 540

Ser Thr Arg Asn Gly Gln Asn Ile His Val Leu Ser Ala Glu Asp Gln
545                 550                 555                 560

Cys Gln Met Glu Thr Glu Asn Ser Val Leu Ser His Ser Ala Lys Val
                565                 570                 575

Ser Pro Ala Glu His Asp Ile Gln Ile Met Ser Asp Leu His Glu Gln
                580                 585                 590

Ser Leu Pro Lys Lys Lys Lys Gln Lys Leu Glu Val Thr Arg Glu
            595                 600                 605

Lys Gln Thr Met Ile Asp Asp Ile Pro Met Asp Ile Val Glu Leu Leu
    610                 615                 620

Ala Lys Asn Gln His Glu Arg Gln Leu Met Thr Glu Thr Asp Cys Ser
625                 630                 635                 640

Asp Ile Asn Arg Ile Gln Ser Lys Thr Thr Ala Asp Asp Cys Val
                645                 650                 655

Ile Val Ala Ala Lys Asp Gly Ser Asp Tyr Ala Ser Ser Val Phe Asp
```

-continued

```
                  660                 665                 670
Thr Asn Ser Gln Gln Lys Ser Leu Ala Ser Gln Ser Thr Gln Lys Glu
            675                 680                 685
Leu Gln Gly His Leu Ala Leu Thr Thr Gln Glu Ser Pro His Pro Gln
        690                 695                 700
Asn Phe Gln Ser Thr Gln Gln Gln Thr His Leu Arg Met Glu Glu
705                 710                 715                 720
Met Val Thr Ile Ala Ala Ser Ser Pro Leu Phe Ser His His Asp Asp
                725                 730                 735
Gln Tyr Ile Ala Glu Ala Pro Thr Glu His Trp Gly Arg Lys Asp Ala
            740                 745                 750
Lys Lys Leu Thr Trp Glu Gln Phe Lys Ala Thr Thr Arg Asn Ser Pro
        755                 760                 765
Ala Ala Thr Cys Gly Ala Gln Phe Arg Pro Gly Ile Gln Ala Val Asp
        770                 775                 780
Leu Thr Ser Thr His Val Met Gly Ser Ser Asn Tyr Ala Ser Arg
785                 790                 795                 800
Gln Pro Val Ile Ala Pro Leu Asp Arg Tyr Ala Glu Arg Ala Val Asn
                805                 810                 815
Gln Val His Ala Arg Asn Phe Pro Ser Thr Ile Ala Thr Met Glu Ala
            820                 825                 830
Ser Lys Leu Cys Asp Arg Arg Asn Ala Gly Gln Val Val Leu Tyr Pro
        835                 840                 845
Lys Glu Ser Met Pro Ala Thr His Leu Leu Arg Met Met Asp Pro Ser
    850                 855                 860
Thr Leu Ala Ser Phe Pro Asn Tyr Gly Thr Ser Ser Arg Asn Gln Met
865                 870                 875                 880
Glu Ser Gln Leu His Asn Ser Gln Tyr Ala His Asn Gln Tyr Lys Gly
                885                 890                 895
Ser Thr Ser Thr Ser Tyr Gly Ser Asn Leu Asn Gly Lys Ile Pro Leu
            900                 905                 910
Thr Phe Glu Asp Leu Ser Arg His Gln Leu His Asp Leu His Arg Pro
        915                 920                 925
Leu Arg Pro His Pro Arg Val Gly Val Leu Gly Ser Leu Leu Gln Lys
    930                 935                 940
Glu Ile Ala Asn Trp Ser Glu Asn Cys Gly Thr Gln Ser Gly Tyr Lys
945                 950                 955                 960
Leu Gly Val Ser Thr Gly Ile Thr Ser His Gln Met Asn Arg Lys Glu
                965                 970                 975
His Phe Glu Ala Leu Asn Ser Gly Met Phe Ser Ala Lys Trp Asn Ala
            980                 985                 990
Leu Gln Leu Gly Ser Val Ser Ser Ala Asp Phe Leu Ser Ala Arg
        995                 1000                1005
Asn Ser Ile Ala Gln Ser Trp Thr Arg Gly Lys Gly Lys Met Val His
    1010                1015                1020
Pro Leu Asp Arg Phe Val Arg Gln Asp Ile Cys Ile Thr Asn Lys Asn
1025                1030                1035                1040
Pro Ala Asp Phe Thr Thr Ile Ser Asn Asp Asn Glu Tyr Met Asp Tyr
                1045                1050                1055
Arg
```

<210> SEQ ID NO 3
<211> LENGTH: 9455

<212> TYPE: DNA
<213> ORGANISM: Oryza sativa

<400> SEQUENCE: 3

```
gatctatcgt tgattggatt tcgctgggct agctaggtag acaagggttc aaaatgtgac      60
gaacattatt gagctaataa ataacgagaa accaacttgg tatataggtc aatttcaaaa     120
gaaacaagct gacaaaattc gtccaatttc actagttttt gtcagtaatt gaatggcaat     180
catggttatc gacaaaaccg cttaggagtg ctatttggtg atggaatggt ttataaaact     240
ttggaccgga gtagcagtac aatggcttgt ctgaacaggc taggtagcat agtaggtcct     300
tttgccttgg ttgcactgtt ctgtcggctt ataggggaat ctattggctt aatggaaggg     360
aaaatagtgt gactagcatc atcgatttgc ttgctatcat gtttgagcat cattgacatg     420
tgggtgtcga tctaggagac tatgaatcta gcgaatcctc actagtatgc acatgcacaa     480
cgacatcatg cagctatatg tacaacaatg taggaatggt agctctactc ggattggtgg     540
ccgcattcct acattgctag aaaaacacaa acacacacac acacacacac aaacaaacat     600
aggacgctgc aacacctctt ccctggctac cactatcgcc aaatgccaag catggttgtg     660
ttgacctccc tccttagctg ccactgtgtc cacttcaaaa tccataacca cgacatcttc     720
ccttcttcta caattgttac tactgttctt gaagaggttc ttgtcctacc gacttactaa     780
agaccaacca ttggtcagca gagcatctcg agacttctat accaaagtaa cattgagagg     840
tcaatggcat gtaggaccat cactccgttt gcattgacca atcagagatg agtctgaaca     900
atttcaaccc gtaaaaacgg tccacaattt gattcatcta ttggtttgct gtctgcccat     960
ggccctgcat cttgattgtt tatgatcttt cttagttatc tcttgagatt taatctacct    1020
aattgtgtca ttttaatcct ttgatttatc ttgattggat tcggtctact ttggtttcac    1080
catcttagcc ccgatatgat cttggtagcc cttttttcct cgcactaatc attttcgatt    1140
ctcgactcca atctaagttc ccatggtaga tttaggtcaa taagtgaaaa acaatttccc    1200
ttacaattta atccccttttt gagtaatgac cttcgtactt cctcaaacga tggtttcatg    1260
gataaagatt tgatatttgt ggcgcacgga tggggcatgg cttatgaaga aaatgagctc    1320
attggattgg tatttctcc tccatgctcc tattggtaaa aatattggtt tagttggata    1380
gtcaggttag aacgggattt aaaaatgtga ctacaactag tcgtttatcg cggttgcaca    1440
tgggtgtcaa cgggtgactg cctgtgttgg catcaataat ttagaattag aggtgtcggc    1500
ttaatgctgg tagattgtgg atatcctccc atacacgtag gcgtcgatgg cttcatgtgc    1560
gtacgtgccg tcctgcatag gatgggtagc aacggaggaa ggctggcttt gttgacttgt    1620
agcctcacta aggccaactg cctattggca atgaagttgt ttttgtttaa ggagaaacaa    1680
acttttgagc taggcaacat cggtatgtag caggccattc tctaggtcaa tggcacttag    1740
agtcggagca tgccggccgt gcctattaca acatggttat catgtgcatg tggcaagggc    1800
acacattaca cgtccccatt gtctaacatc gtagactatg agtttgatag aagaaaccca    1860
actgaaaggt cagtgtcaaa tccattctac ctgtgtcgag aactaaggtt aagcgtttta    1920
tatagattag gacactcaca tacatatgct gtgcatgggg tggtgagagc cattatgtac    1980
cactagtgac atgtgtctac ctagtttatt gatctattga ttgaaaattc gactgagata    2040
agaataacta tgtggtatat ttaacttggt acaacatata gtggttggaa catcacatta    2100
gacatgcctt ggcaggaaga aagccgctgt agtttaattt aacatgttaa acaccacata    2160
gtgagtaatc aatctaggct taaaaaaaat aaagacaaca caaacaaaca cagagaacac    2220
```

-continued

```
ataaacacag aggggcaat caactctgtt gtttgatcta tacttcgtca gagtttgata      2280
tatctctgct ctctgcattt taaaactact tatattacaa agcactgtat gttatatagt      2340
aatactttgt agatcacgag tataaaacac agataggtac aattttttt actcctacgt       2400 atttacgtat taaccggtac aatattattt agcatgcatg tacgcgtgat attagagtgg      2460
agtatactac ctacgcatgc tcgggcagta tcggtacctc tatacctacc tatatacaca     2520
taccaggtag agtacagcgg caggtagagt acacagtagt atatggagct tattttatca     2580
tttttattac tggagataga agaagaagag aaaggagaga gagagagaaa gagtggaagg     2640
gaaaggcgtg cggggcccac acacgcagca gggcagcgct gcggaggtga ggtgagggca     2700
ggggcagggg cagggcggac tggccaacgc caactccaac tccaactccc gtacaaataa     2760
aatatacaat cctttctttt tcctcctcct cttttccctt ccattccacc ccctctctc      2820 tctcttctcc actccaaatc ccttcttacc ctattccct cccccgcag cttctcttcc       2880 tcctgcagta ctcgccgcca ccaccaccgc gccgccgccg ccggccgcgt tccgagaccc     2940
actcgatcgg aatccaccgc ggcgcgcccg cgcgcctgcg tcctcttcct tccccgggag     3000
ccgaccgacc acgcgaccca gtcgatctcc ctctccgggc gccaaccgcg tcttagcttc     3060
atcgaatcca ccgccccacc ccgcatctcc tcctcctcct ccgacgacga cgactactac     3120
tagtcttctc caataagccc ccctcccgct cccccgcct gaagaagaag cagcagctag      3180
ctccggggag aggtcgacgg cgcgccgggt agatcgcgcc ccgccccgcc tgcgtcgcgg     3240
ctgtcggagc aaacgcaaac cccccaggta atcaacgaac ttttcctccg ccgcaagaac     3300
agctcccgcg gggggtttgg ttttgaccga tttcttcccc cctcccccca aatcgaccca     3360
tccaatttcg cctcgattta cttccgattt ccccactttt ttttcttcct ttcgggttgg     3420
ggggttgcgg ttttggggga ggagagggt tcagctcatc cgaagcccca cgttaggtcc      3480
gccccctttc cagctgtgcc cctctctcgg gcctcgagct cctcgcctcc atgggaacca     3540
aagcccttat atttcatgtc gcggaagaaa aaaaaatccc gtcttttgcg gggatcctcg     3600
cggctacgta cgagcctag ttaccgcgcg gattttagtt acggcggttt atgcggcccc     3660
tccctctagg ttttagatct acccatctct ctctctctct ctctctctct ctctgtgcat    3720
gcatgtgtct atcttagcta tacctgtatt atttggaagg ttaattatgg ttgtgtatat     3780
gtggcgcggt aattaattag tttaattcgc accccctctc tctttgttta tctaggtttt    3840 gggaattt atttcttgct ataattttgc ccgctcgaat ttctggtgct cttatattcc       3900
atgagctgat tgaagtggat atatattgtg cgtgcgtgcg tgctattgct acatcggctt     3960
gacttcttct tgcctactac ttcattaatt tgtttcttct ggtttctgtt tcaggttgtt     4020
ctagcgtgtg cagcggctag ctgattgatt gtcttctgtg atatatccag agctcgtgtt     4080
ttgtggtttg tggtttgtgg tttgtgcttg gattgttgat gtgctaattc gcggcgttac     4140
aagatcactg ctggattgat attgagttgt gcctcggctg tgctagctgt gtgttgattc     4200
tctcctcgtc gtggtgatcg atatggagat tgttgcagta gatcaggagg gagctcgtgt    4260
tgttgggacg aactgtatgc ttgctcgtgg tggaactggt gctgtagcgc cagtgttgga     4320
gctgacagcg acgcctcgtc aggatgcagc cgctgaagct ggtgtagacg aaccggcaca     4380
acaccaatgc gagcatttct ccataaggta atcatttct gtatttccaa ttccagtatc      4440
gcgttgtgga tgaataatga atcggcatgt catgccatat tgcactgttt gatggaagag     4500
tatgattgat cgtggttttt gcacagtttg ctgttgggac ttatatggtc atctgttttg     4560
tacgatcgta tacactgggt cgacatgctt atgactttgg ttcgatttag gaagtcaata    4620
```

-continued

```
catccactac tagctctata tctagccatg tgaactcatt tatgccatag cacagctagc    4680
aggctagcag caaaaaatat atataatatt tgcatatatg ttggtgtttc atgtatcttt    4740
atactctacg tacatccatt aatatcttca atgtatgaat ctgagcacat gattgtgagt    4800
gctacacata tgcatgtctg tatgtgtgtt cattaggtgt ttgatcatat ttgtttgtgt    4860
tggggtgcgc atgcatttat tcaggccatg ctgtaggctg tagctagata tttgtgtttg    4920
tatattattt ctgttgaaca agctgattac taatgaaatt aaccttttg gggtacactc     4980 atatattggg ccctacattt ttgtaatcat ttttcctttg tgctgaggtt cagcataaaa    5040
cttttttatc ataagcatgt ttacatccta ggagattctt agaactgatg gtttcttcat    5100
atttgcatta tgtttgattt gatagtccat tattatttta agccttttca attgtttaga    5160
gattctagag atgatatata tcaaccatag acttgtcacg ttttggttta atactttcta    5220
gaactaatta gattattatt tttgtagttt atcctgtcat gctatttgta ttatctttga    5280
attcaaactg caatacttag attatcttga aggtcctctt tttctggact gtacaagcta    5340
tgtatgaaat gcctacctcc cagcatcctt tagattatgt agggccttt ctgagtttat      5400 cagttgtata ttgactgaag cacgcaatgt gctatatata tgtgccatgc atctttataa    5460
tgataatctt attttcttg taccagaggg tatgttgctc ttcttcagaa gaaggatcca      5520
aaattctgct ctctatctcg gattttccat gaccagaaaa aatgtgatga acacaaagct    5580
agttcaagcc cattttctgt agcaaagttt cgacgatggg attgctcgaa gtgcttggat    5640
aagttgaaaa cttcagataa tggaacagca ccaagaactc ttcccgcaaa gcagaatggc    5700
acaagtgatg gttgctccat cacatttgtt cggagcactt ttgtgcctgc tagtgttggt    5760
tcccaaaaag tgtctcctag cacacaatca tctcaaggga agaatgctga tagatcaact    5820
cttccaaaga gtgtgcaaga aggcaatgac tccaaatgca atgcgccttc tggcaagaat    5880
ggagctgctg aggccaatac tgattccacc atgaaaggta tggtagatgt agagcctttc    5940
aaattcctaa gtaggatttt atttaaggta tagaataaac taatgtttgt gtgattttct    6000
cagatttgca agggccagcc caaaattatg atgtggcagc aaatgtctct gaggacaaca    6060
cttctgttga tgttggggct ttacctgaag ttccccagat tacatggcac atagaagtaa    6120
atggtgcaga tcaacctcca tccactccaa aactttctga agtggtcctc aaaagaaatg    6180
aagatgaaaa tggaaaaact gaagagactc ttgttgctga gcagtgcaat ttgaccaaag    6240
atcctaaccc aatgtctgga aaggaacgtg atcaggttgc tgagcagtgc aatttgacca    6300
aagatccgaa accagtgtct gggcagaaat gtgagcagat ctgcaatgag ccatgtgaag    6360
aagttgttct caaaagaagc tccaaatcta agaggaagac ggataagaag ttgatgaaga    6420
agcagcagca cagcaagaaa cgcactgccc aggctgatgt ttcagatgca aagctttgtc    6480
ggagaaagcc aaaaaaggtg cggcttctat cagaaattat aaatgctaac caggttgagg    6540
attctagaag tgacgaagtt catcgtgaaa atgccgctga tccctgtgag gatgatagaa    6600
gtaccatccc ggtcccgatg gaagtaagca tggatattcc tgttagcaac catacagtgg    6660
gagaagatgg gttaaaatca agtaagaaca agacaaaacg caaatactct gatgttgtag    6720
atgatggatc atcacttatg aactggctga atggaaaaaa gaaagaact ggaagtgtgc      6780 atcacacagt tgctcatcca gctgggaatt tgagcaacaa aaaagtgaca cccactgcga    6840
gtactcagca tgatgatgag aatgatactg aaaatggtct tgacacaaat atgcataaga    6900
cagatgtctg tcagcatgta tcagaaatct ccacacagag gtgctcatca aagggaaaa     6960
```

```
cagcgggttt gagtaagggg aaaacacatt cagctgctag taccaaatat ggtggtgaaa   7020
gcaccagaaa tggtcagaac atacatgtac tcagcgcaga agatcaatgc cagatggaaa   7080
ccgaaaactc tgttctgagt cactcggcaa aggtacgaat tttgtgaatc atgaggaatt   7140 tttgctttt aaattgactg aatcaacatt tatctgtatg aaggaataat attggtgcat    7200
aacaatgtta agaaatatgc atacaatgtt tatttatatg ctttccactg ttcttcttta   7260
cttatgtttt gatactcttt tgtgtgtgc gtgcatgtgt gcatgtgtgt gtgtgtgtgt    7320
gtgtgcgcgc gtgtgtgtgc acgtgcgtgg cgcaatattc ttttttagac tcatattata   7380
gtgattgtaa tggactgaca ttttcctcat ttctcatctc aggtttctcc agctgagcat   7440
gatatccaaa ttatgtctga ccttcatgag cagagtctac ccaagaagaa aagaagcaa    7500 aaacttgaag tgactcgtga aaaacagacc atgatagatg acatccccat ggatattgtt   7560
gaactgctag ctaaaaacca gcatgagagg cagcttatga ctgagactga ttgttctgac   7620
atcaaccgta ttcaatccaa gacaactgct gatgatgatt gtgtaatagt agctgccaag   7680
gatggttcag attatgcatc aagtgtgttt gacactaatt cccaacagaa gtccttggca   7740
tcccaaagta cacagaagga gttacagggt catttggcat tgaccacaca agagtctcca   7800
catcctcaga actttcagtc tactcaggaa cagcagacac atttgcggat ggaagaaatg   7860
gtcactattg ctgcaagctc accactattt tcacatcatg atgatcagta tattgctgaa   7920
gcaccaactg aacattgggg ccgtaaggac gcaaagaagc taacgtggga gcaatttaag   7980
gccactacaa gaaattctcc agcagcaaca tgtggtgctc aatttagacc tggtatccaa   8040
gcagttgact tgacttctac tcatgtcatg ggatcttcca gcaattatgc atctcgccaa   8100
ccagtaattg cgccactgga ccgctatgct gaaagagcgg ttaaccaggt ccatgcaaga   8160
aattttccaa gcacaatagc aaccatggaa gcgagtaagt tatgtgatcg gagaaatgct   8220
ggacaagtag tcttgtatcc taaagaatcc atgcctgcga cgcatcttct gagaatgatg   8280
gatccatcaa cattagcaag cttccccaac tatggaactt ctagcaggaa ccagatggag   8340
tctcaacttc ataattctca gtatgcacat aatcagtaca aaggatcaac cagcacatca   8400
tatggcagta acctgaatgg aaagattcca ttgacattcg aagacttatc acggcatcag   8460
ctgcatgatc tgcacagacc tttacgccca catcctagag ttggtgtgct tggctccttg   8520
ctgcagaagg aaattgcaaa ctggtcggag aactgtggca cacaatctgg ttataagtta   8580
ggagtgtcaa caggaataac atcgcatcag atgaacagaa aggaacattt tgaagccctg   8640
aattctggaa tgttttcagc aaaatggaat gcattgcagt tgggttctgt tagctccagt   8700
gcagattttt tatcagcgag gaacagcata gctcaatctt ggaccagagg caagggtaaa   8760
atggttcatc ccttggatcg gtttgtgaga caggatatct gtataactaa caagaaccca   8820 gctgattta ctacaatcag taacgataac gagtatatgg attaccgctg aagcagaaag   8880
tggtgtgcat aattcctgaa catttacaat catacatttc atctttatgg cgccaaatag   8940
tcatactgta agaggagggc tttgctggat ctgctgtaag gtaagttgaa cttttcttc    9000 ttgcaagttt atcagtttaa gaaaaaagaa tgattactta tgttagcaag gatggttctt   9060
gcaggcttct tgtaagttgt ggatgcccca ttttctggat gggaacctgc cagacagtga   9120
acaagggctt tgcaaggtgc agcatccggt ttttgttttg ccagtccaag aaacgtcctc   9180
ctgttacttt gtagttgtac tcatactagt gcgcttgttt gtacaaggag aaatgtgtaa   9240
ccttgttgaa aaaatgtctc ccccattttg taattaccat aaggaggttt atagtgttgt   9300
gagctgtgtg tgactgacgg cgagaaatgg ttttgtcggt gttaaggttg aaacgactag   9360
```

-continued

```
ctctcgttat caatgtgttg taaacttcta gattgatgtg ttaccttact cttgaagtca      9420
acaccggaga atttacagta cttttttgcc gtgcc                                 9455

<210> SEQ ID NO 4
<211> LENGTH: 26
<212> TYPE: DNA
<213> ORGANISM: Oryza sativa

<400> SEQUENCE: 4
gagagcatca tcggttacat cttctc                                           26

<210> SEQ ID NO 5
<211> LENGTH: 24
<212> TYPE: DNA
<213> ORGANISM: Oryza sativa

<400> SEQUENCE: 5
tctagcagtc tcaatgatgt ggcg                                             24
```

GENE INVOLVED IN BRASSINOSTEROID RESPONSES

BACKGROUND OF THE INVENTION

1. Field of the Invention

The present invention relates to a novel gene. In particular, the present invention relates to a novel gene in plants which encodes a protein having the function of controlling an in-vivo signal transduction system in a physiological reaction system against brassinosteroid hormone.

2. Description of the Related Art

Transposons are mutagenic genes which are known to be ubiquitous in animal, yeast, bacterial, and plant genomes. Transposons are classified into two classes, Class I and Class II, depending on their transposition mechanisms. Transposons belonging to Class II are transposed in the form of DNAs without being replicated. Known Class II transposons include the Ac/Ds, Spm/dSpm and Mu elements of *Zea mays* (Fedoroff, 1989, Cell 56, 181–191; Fedoroff et al., 1983, Cell 35, 235–242; Schiefelbein et al., 1985, Proc. Natl. Acad. Sci. USA 82, 4783–4787), and the Tam element of *Antirrhinum majus* (Bonas et al., 1984, EMBO J., 3, 1015–1019). Class II transposons are widely used for gene isolation techniques which utilize transposon tagging. Such techniques utilize the fact that a transposon induces physiological and morphological changes when inserted into genes. The affected gene can be isolated by detecting such changes (Bancroft et al., 1993, The Plant Cell, 5, 631–638; Colasanti et al., 1998, Cell, 93, 593–603; Gray et al., 1997, Cell, 89, 25–31; Keddie et al., 1998, The Plant Cell, 10, 877–887; Whitham et al., 1994, Cell, 78, 1101–1115).

Transposons belonging to Class I, also referred to as retrotransposons, are replicated and transposed via RNA intermediates. Class I transposons were first identified and characterized in *Drosophila* and in yeasts. However, recent studies have revealed that Class I transposons are ubiquitous in plant genomes and account for a substantial portion of the genomes (Bennetzen, 1996, Trends Microbiolo., 4, 347–353: Voytas, 1996, Science, 274, 737–738). A large majority of retrotransposons appear to be inactive. Recent studies indicate that some of these retrotransposons are activated under stress conditions such as injuries, pathogenic attacks, or cell culture (Grandbastien, 1998, Trends in Plant Science, 3, 181–187; Wessler, 1996, Curr. Biol. 6, 959–961; Wessler et al., 1995, Curr. Opin. Genet. Devel. 5, 814–821). Activation under stress conditions has been reported for Tnt1A and Tto1 in tobacco (Pouteau et al., 1994, Plant J., 5, 535–542; Takeda et al., 1988, Plant Mol. Biol., 36, 365–376), and Tos17 in rice (Hirochika et al., 1996, Proc. Natl. Acad. Sci. USA, 93, 7783–7788), for example.

The Tos17 retrotransposon of rice is one of the most-extensively studied plant Class I elements in plants. Tos17 was cloned by an RT-PCR method using a degenerate primer prepared based on a conservative amino acid sequence in reverse transcription enzyme domains between Ty1-copia retroelements (Hirochika et al., 1992, Mol. Gen. Genet., 233, 209–216). Tos17 is 4.3 kb long, and has two 138 bp LTRs (long chain terminal repetitions) and PBS (primer binding sites) complementary to the 3' end of the start methionine tRNA (Hirochika et al., 1996, supra). Tos17 transcription is strongly activated through tissue culture, and its copy number increases with culture time. In Nipponbare, a model *Japonica* cultivar used for genome analysis, two copies of Tos17 are initially present, which are increased to 5 to 30 copies in a regenerated plant after tissue culture (Hirochika et al., 1996, supra). Unlike Class II transposons which were characterized in yeasts and *Drosophila*, Tos17 is transposed in chromosomes in random manners and causes stable mutation, and therefore provides a powerful tool for functional analysis of rice genes (Hirochika, 1997, Plant Mol. Biol. 35, 231–240; 1999, Molecular Biology of Rice (ed. by K. Shimamoto, Springer-Verlag, 43–58).

SUMMARY OF THE INVENTION

The present invention relates to a polynucleotide encoding a plant gene capable of controlling a signal transduction system for brassinosteroid hormone, the polynucleotide encoding an amino acid sequence from Met at position 1 to Arg at position 1057 of SEQ ID NO: 2 in the SEQUENCE LISTING, including any polynucleotide encoding an amino acid sequence in which one or more amino acids are deleted, substituted or added to the amino acid sequence.

In one embodiment of the invention, the polynucleotide may be derived from rice.

In another embodiment of the invention, the polynucleotide may be as represented by SEQ ID NO: 1 in the SEQUENCE LISTING.

The present invention further relates to methods for controlling various effects in plants in which brassinosteroid hormone is involved, e.g., growth promotion, yield increase, quality improvement, maturation enhancement, and tolerance against biotic and abiotic stresses.

The inventors diligently conducted systematic analyses of phenotypes of plants having a newly transposed To17 copy and sequences adjoining Tos17 target sites with respect to rice. As a result, the inventors found a dwarf rice mutation obtained from Tos17 insertion, and isolated the gene responsible for this mutation by utilizing Tos17 as a tag, thereby accomplishing the present invention.

Thus, the invention described herein makes possible the advantage of providing a novel plant gene which can be provided by using Tos17.

This and other advantages of the present invention will become apparent to those skilled in the art upon reading and understanding the following detailed description with reference to the accompanying figures.

BRIEF DESCRIPTION OF THE DRAWINGS

FIGS. 1A and 1B are photographs showing a brassinosteroid non-sensitive mutant having Tos17 inserted therein, which was found among regenerated Akitakomachi lineage. On the left of each figure is shown a brassinosteroid non-sensitive mutant having Tos17 inserted therein. On the right of each figure is shown a wild type plant body. FIG. 1A evidences an influence toward dwarfism and upright form. FIG. 1B evidences an influence toward malformation of grain hulls.

FIGS. 2A and 2B are photographs showing a brassinosteroid non-sensitive mutant having Tos17 inserted therein, which was found among regenerated Nipponbare lineage. On the left of each figure is shown a brassinosteroid non-sensitive mutant having Tos17 inserted therein. On the right of each figure is shown a wild type plant body. FIG. 2A evidences an influence toward dwarfism and upright form. FIG. 2B evidences an influence toward malformation of grain hulls.

FIG. 4 shows the amino acid sequence (SEQ ID NO: 2) of the novel rice gene which controls a physiological reaction system induced by brassinosteroid hormone, together with characteristic sequences found therein (where nuclear localization signals and an ATP/GTP binding motif can be observed).

DESCRIPTION OF THE PREFERRED EMBODIMENTS

Figure 3A:
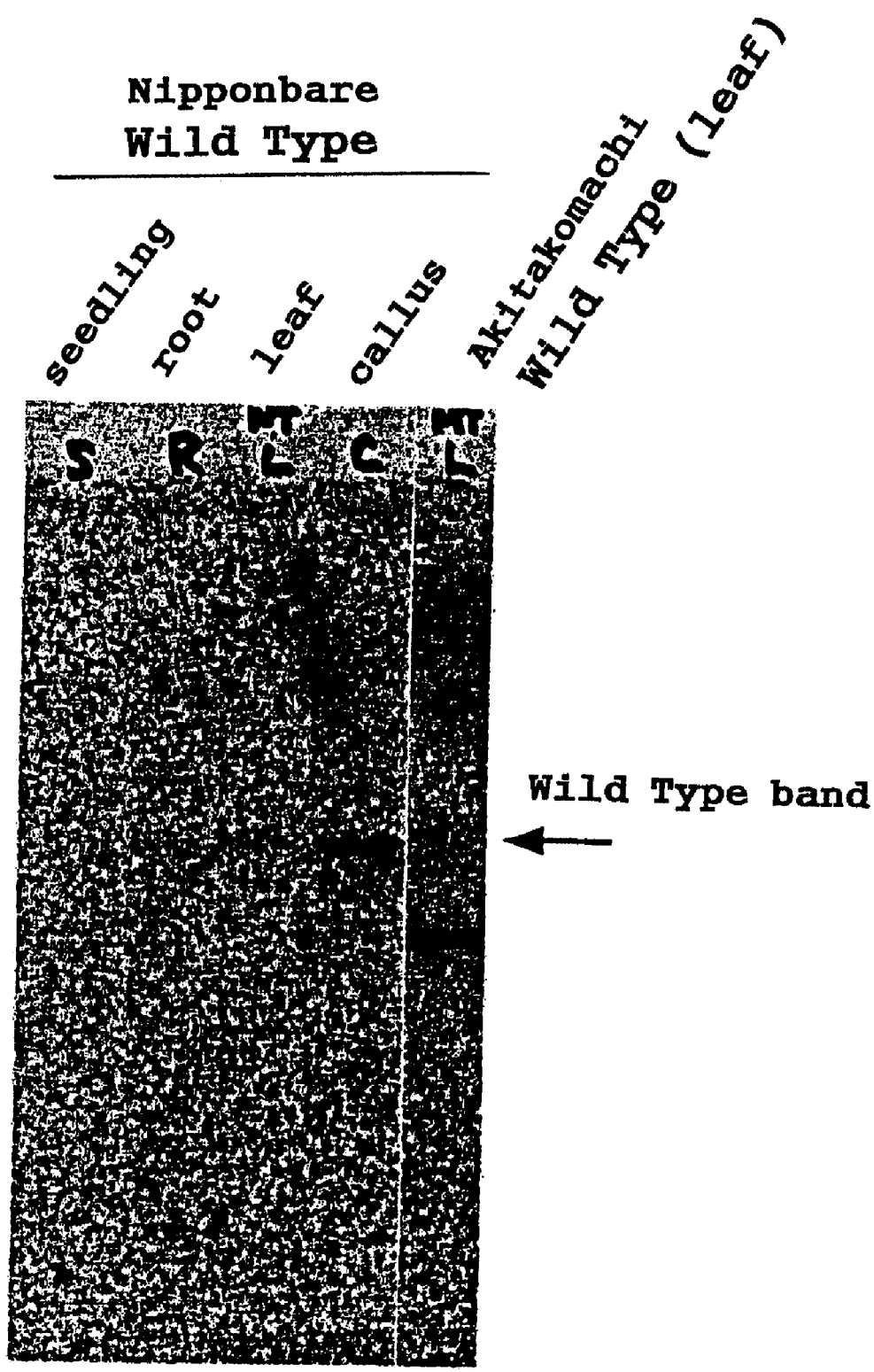
FIG. 3A shows a Northern analysis autoradiogram of RNA extracted from the leaves of a brassinosteroid non-sensitive mutant (Akitakomachi) and RNA extracted from various organs of a wild type rice plant (Nipponbare).

The present invention provides a method for producing an improved plant, the method utilizing a novel plant gene which can be provided by using Tos17.

According to the present invention, there is provided a polynucleotide encoding a plant gene capable of controlling various effects in which brassinosteroid hormone is involved. As used herein, the term "capable of controlling various effects" means the ability to control various effects in plants in which brassinosteroid hormone is involved, e.g., growth promotion, yield increase, quality improvement, maturation enhancement, and tolerance against biotic and abiotic stresses, including dwarfism, upright form, and malformation of grain hulls, thereby providing a number of agriculturally useful effects as are attained by treatments with brassinosteroid hormone agricultural chemicals. The term "plants" encompasses both monocotyledons and dicotyledons.

A polynucleotide encoding a plant gene capable of controlling a signal transduction system for brassinosteroid hormone according to the present invention is, for example, a polynucleotide encoding an amino acid sequence from Met at position 1 to Arg at position 1057 of SEQ ID NO: 2 in the SEQUENCE LISTING, including any polynucleotide encoding an amino acid sequence in which one or more amino acids are deleted, substituted or added to the aforementioned amino acid sequence.

A polynucleotide encoding a plant gene capable of controlling various effects in which brassinosteroid hormone is involved encompasses any polynucleotides which have at least about 80% sequence homology, preferably at least about 85% sequence homology, and more preferably at least about 90% sequence homology, still more preferably at least about 95% sequence homology, and most preferably at least about 99% sequence homology, with an amino acid sequence from Met at position 1 to Arg at position 1057 of SEQ ID NO: 2 in the SEQUENCE LISTING, so long as they are capable of controlling various effects in plants in which brassinosteroid hormone is involved. The term "sequence homology" indicates a degree of identity between two polynucleotide sequences to be compared with each other. The rate (%) of sequence homology between two polynucleotide sequences for comparison is calculated by, after optimally aligning the two polynucleotide sequences for comparison, obtaining a matched position number indicating the number of positions at which identical ("matched") nucleic acid bases (e.g., A, T, C, G, U, or I) are present in both sequences, dividing the matched position number by total number of bases in the polynucleotide sequences for comparison, and multiplying the quotient by 100. The sequence homology can be calculated by using the following sequencing tools, for example: a Unix base program designated GCG Wisconsin Package (Program Manual for the Wisconsin Package, Version 8, September 1994, Genetics Computer Group, 575 Science Drive Madison, Wis., USA 53711; Rice, P. (1996) Program Manual for EGCG Package, Peter Rice, The Sanger Centre, Hinxton Hall, Cambridge, CB10 1RQ, England), and the ExPASy World Wide Web molecular biology server (Geneva University Hospital and University of Geneva, Geneva, Switzerland).

Cells into which genes have been introduced are first selected based on drug resistance, e.g., hygromycin resistance, and then regenerated into plant bodies by using usual methods.

The terminology and laboratory procedures described throughout the present specification are directed to those which are well-known and commonly employed in the art. Standard techniques may be used for recombination methods, polynucleotide synthesis, microorganisms culturing, and transformation (e.g., electroporation). Such techniques and procedures are generally known from various standard textbooks available in the field or by way of the present specification (including a generally-referenced textbook by Sambrook et al., Molecular Cloning: A Laboratory Manual, 2nd edition (1989) Cold Spring Harbor Laboratory Press, Cold Spring Harbor, N.Y.). Such literature is incorporated herein by reference.

The polynucleotide according to the present invention can be obtained by using the method described herein, for example. However, the polynucleotide according to the present invention may also be obtained by any chemical synthesis process based on the sequence disclosed herein. For example, the polynucleotide according to the present invention may be synthesized by using a polynucleotide synthesizer available from Applied Bio Systems in accordance with the instructions provided by the manufacturer.

Methods of PCR amplification are well-known in the art (PCR Technology: Principles and Applications for DNA Amplification, ed. H A Erlich, Freeman Press, NewYork, N.Y. (1992); PCR Protocols: A Guide to Methods and Applications, Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, McPherson, Quirkes, and Taylor, IRL Press, Oxford). Such literature is incorporated herein by reference.

EXAMPLES

Hereinafter, the present invention will be described by way of examples which are of illustrative but non-limiting nature.

Example 1

Activation of Tos17 Via Culture

Using fully ripened seeds of Nipponbare and Akitakomachi, which are varieties of *Japonica* subspecies, induction of calli and cell suspension culture were carried out as described earlier (Hirochika et al., 1996, supra). The activation of Tos17 which was used for gene destruction was carried out following the method of Ohtsuki (1990) Yoshiaki Ohtsuki, "Video Manual for Experiments in Rice Protoplast Culture System," published by Food and Agricultural Research Development Association, Tokyo, Japan (1990)). In summary, fully ripened seeds of rice were cultured in an MS medium having 2,4-dichlorophenoxyacetic acid (2,4-D) added thereto (2 mg/ml) (Ohtsuki (1990), supra) (25° C., 1 month), to induce callus formation. The resultant calluses were cultured for 5 months in an N6 liquid medium having 2,4-D added thereto (Ohtsuki (1990), supra), and thereafter placed on a redifferentiation medium (Ohtsuki (1990), supra), whereby redifferentiated rice plants were obtained (first generation (R1) plants).

Example 2

Isolation of Sequences Adjoining Tos17

Utilizing each of the regenerated R1 rice plants obtained according to Example 1 as a first strain, about 1000 R1 seeds were collected from each strain and grown on a paddy field to obtain second generation (R2) plants, which were subjected to a morphological analysis. As a result of observing the phenotypes of the respective plant bodies in the R2 group, it was learned that about ¼ of the R2 group of an Akitakomachi strain A0369 exhibit the "dwarfism, upright form, and malformation of grain hulls" phenotype (FIGS. 1A and 1B). In the regenerated group of Akitakomachi, dwarfism, upright form, and malformation of grain hulls were observed for brassinosteroid insensitive mutants (FIG. 1A, left, and FIG. 1B, left), as compared with the wild type (FIG. 1A, right, and FIG. 1B, right). The isolation of adjacent sequences of transposed Tos17, which is co-segregating with the phenotypes, was carried out by an IPCR method (Ochman et al., Genetics November; 120(3): 621–3 (1988) and Triglia et al., Nucleic Acids Res August 25; (16): 8186(1988)). The total DNA of A0369 was digested with XbaI, and a ligation process was performed in a large quantity of solution, thereby obtaining self-ligated circular molecules. In the self-ligated circular molecules, the adjacent sequences are flanking the internal sequence of Tos17. As a result, amplification was successfully carried out by usual PCR methods using an outward primer pair (T17TAIL3: GAGAGCATCATCGGTTACATCTTCTC (SEQ ID NO: 4); T17-1950R: TCTAGCAGTCTCAAT-GATGTGGCG (SEQ ID NO: 5)) based on the known sequence of Tos17.

Example 3

Search for Alleles

Using the sequence obtained according to Example 2, lineage in which Tos17 had been inserted at a different site in the same gene was selected by PCR from the regenerated rice group of Nipponbare. As a result, a line (NC6148) which similarly exhibited dwarfism, upright form, and malformation of grain hulls were observed for brassinosteroid was selected. That is, in the regenerated rice group of Nipponbare, as well, dwarfism, upright form, and malformation of grain hulls were observed for brassinosteroid insensitive mutants (FIG. 2A, left, and FIG. 2B, left), relative to the wild type (FIG. 2A, right, and FIG. 2B, right). It was concluded that these common mutations were results of the same gene having been destroyed.

Example 4

Expression and Analysis of the Causative Gene

Figure 3B:
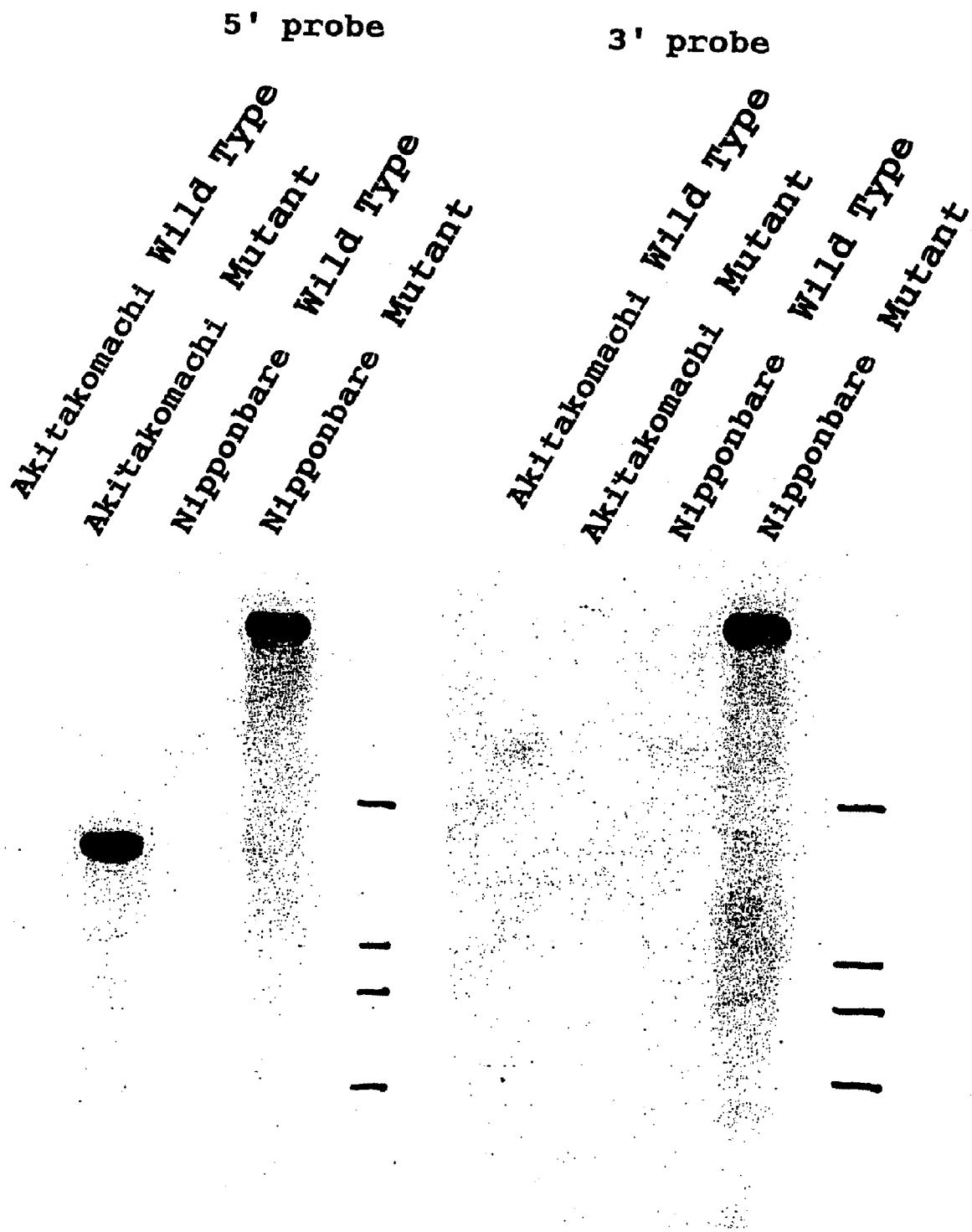
FIG. 3B shows a Northern analysis autoradiogram of RNA extracted from brassinosteroid non-sensitive mutants and RNA extracted from wild type rice plants. The left-hand side of FIG. 3B shows a comparison between wild types and mutants obtained by using a 5' probe. The right-hand side of FIG. 3B shows a comparison between wild types and mutants obtained by using a 3' probe.

From the group of R2 rice plants (selfed progeny from the A0369 and NC6148 strains) obtained according to Examples 2 and 3, individuals exhibiting mutation were identified from normal individuals. RNA was prepared from both groups of individuals, and the expression specificity was analyzed through Northern analysis. After agarose electrophoresis, the RNA obtained from individuals exhibiting mutation and the RNA obtained from normal individuals were allowed to adsorb to nylon membranes. DNA fragments which were obtained by amplifying via PCR a sequence (positions 5775–6638 of the genomic sequence) on the 5' side and a sequence (positions 8175–8765 of the genomic sequence) on the 3' side of the Tos17 insertion site in both mutated lines were labeled with $^{32}$P-dCTP. By using these as probes, expression specificity was analyzed through Northern analysis (FIGS. 3A and 3B). As seen from the Northern analysis autoradiogram shown in FIG. 3A, a band (about 4.3 kb) indicated by an arrow was confirmed to be expressed in all observed organs of the wild type. However, in the mutants, transcripts of abnormal sizes were observed due to the insertion of Tos17, indicating that the natural function of the wild type is lost (FIG. 3B).

Example 5

Structural Analysis of the Causative Gene

Using the sequence obtained according to Example 2 as a probe, the corresponding cDNA and genomic clone were obtained from a cDNA library and a genomic library. Their structures are shown in SEQ ID Nos: 1 and 3. It was learned that this gene includes 6 exons and 5 introns, encoding 1057 amino acids, and that Tos17 had been inserted at the 4th and 5th exons in two mutants, respectively. Moreover, motif search results suggested the presence of nuclear localization signal 1 (amino acid residues 329–367 of SEQ ID NO: 2, Robbins & Dingwall consensus sequence; a search result by PSORT program) and nuclear localization signal 2 (amino acid residues 457–460, 595–600 of SEQ ID NO: 2, 4 amino acid nuclear localization pattern signal; a search result by PSORT program) as well as the presence of an ATP/GTP binding domain (amino acid residues 526–533 of SEQ ID NO: 2; a search result by a motif search service on Genomenet). Thus, the possibility of this gene being involved in signal transduction was suggested (FIG. 4).

Example 6

Brassinosteroid Sensitivity Evaluation

Figure 5A:
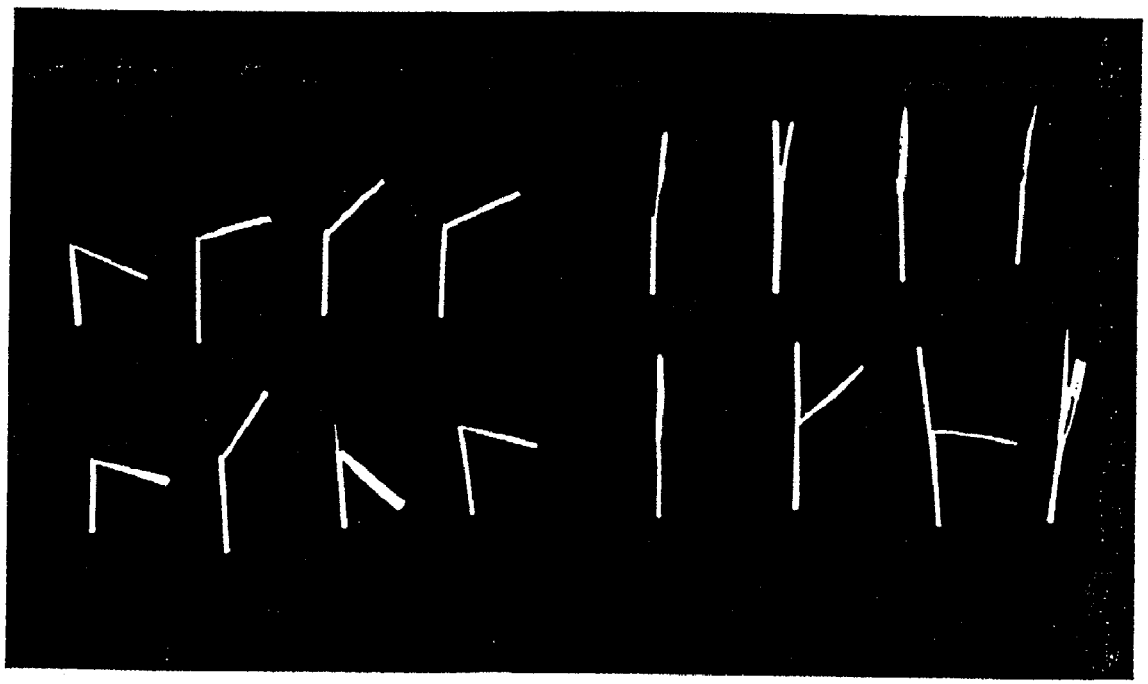
FIG. 5A shows a brassinosteroid leaf blade bending experimentation using a mutated line (A0369) derived from Akitakomachi. The left-hand side shows results of wild type plants, whereas the right-hand side shows results of mutants.
Figure 5B:
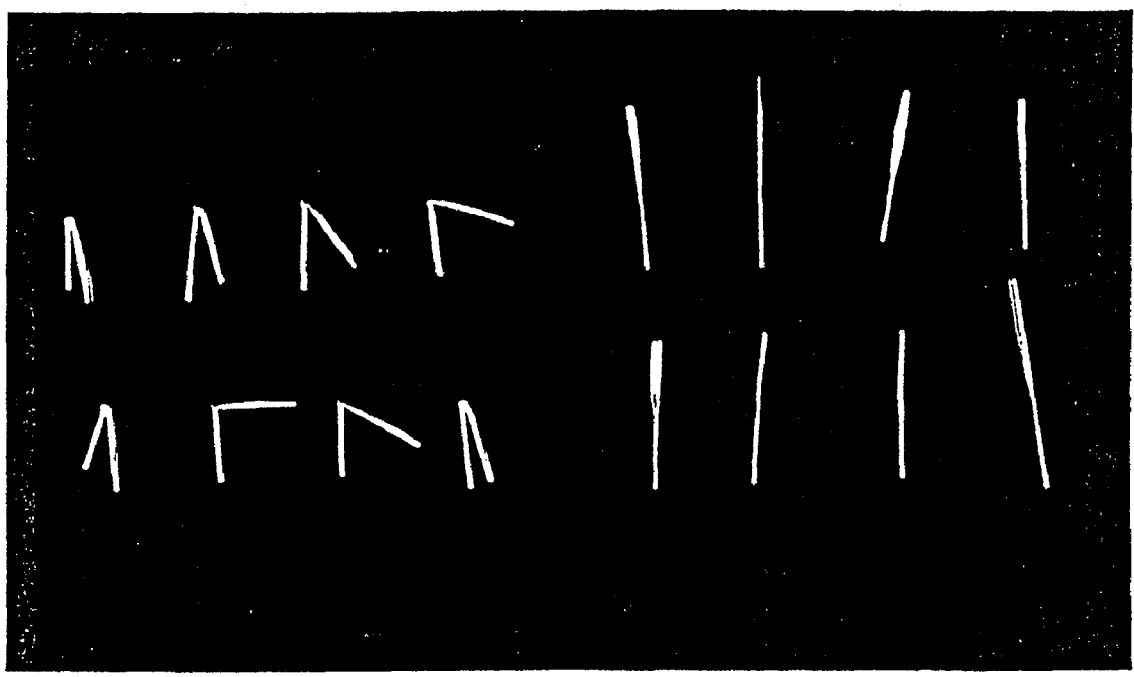
FIG. 5B shows a brassinosteroid leaf blade bending experimentation using a mutated line (NC6148) derived from Nipponbare. The left-hand side shows results of wild type plants, whereas the right-hand side shows results of mutants.

The present gene was deduced to be a factor involved in the signal transduction system for plant hormones, taking note of the facts that the present gene was expressed in all plant bodies and that pleiotropic influences resulted from destroying this gene, as well as the possibility that the gene might be a factor involved in the signal transduction system. Presuming that the signal transduction system is that for brassinosteroid hormone in view of the resultant upright form, the inventors performed a leaf blade bend response test as a brassinosteroid response test, by using brassinolide, which is one kind of brassinosteroid hormone. The second leaf of rice which was allowed to germinate in the dark was cut off, and immersed in a 1 ng/ml of brassinosteroid solution for 48 hours. The wild type individuals having the wild type genes showed bending of the leaf blades and leaf sheath junctions (left-hand side in FIGS. 5A and 5B), showing response to brassinolide, whereas mutant individuals showed little bending thereof (right-hand side in FIGS. 5A and 5B), indicating that the destruction of the present gene resulted in the loss of response to brassinosteroid. From the above results, it was revealed that the present gene is a gene involved in the signal transduction system for brassinosteroid hormone.

The above examples are illustrative, and by no means limiting, of various aspects of the present invention and the manners in which the oligonucleotide according to the present invention can be made and utilized.

Thus, according to the present invention, a novel polynucleotide is provided which is capable of controlling various effects in which brassinosteroid hormone is involved, the polynucleotide being of use in plant breeding. By introducing the present polynucleotide into plants and artificially controlling various effects in which brassinosteroid hormone is involved, it is expected that effects such as growth promotion, yield increase, quality improvement, maturation enhancement, and tolerance against biotic and abiotic stresses can be controlled, thereby providing a number of agriculturally useful effects as are attained by treatments with brassinosteroid hormone agricultural chemicals.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An isolated polynucleotide encoding a plant polypeptide involved in a signal transduction system for brassinosteroid hormone, said polypeptide consisting of the amino acid sequence from Met at position 1 to Arg at position 1057 of SEQ ID NO:2, wherein a plant which has a defect in said polynucleotide exhibits dwarfism, upright form, malformation of grain hulls, and said plant is brassinosteroid insensitive.

2. The polynucleotide according to claim 1, wherein said polynucleotide comprises the nucleic acid sequence from position 655 to position 3825 of SEQ ID NO:1.

* * * * *